United States Patent
Schoenbrunner et al.

(10) Patent No.: US 10,422,012 B2
(45) Date of Patent: Sep. 24, 2019

(54) DEVICES COMPRISING BACTERIOPHAGE PHI6 INTERNAL CONTROL COMPOSITIONS

(71) Applicant: Roche Molecular Systems, Inc., Pleasanton, CA (US)

(72) Inventors: Nancy Schoenbrunner, Charlestown, MA (US); Kwame Sefah, Boylston, MA (US); Yu Tian, Westwood, MA (US); Fangnian Wang, Millis, MA (US); Karen Wang, Natick, MA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 82 days.

(21) Appl. No.: 15/727,116

(22) Filed: Oct. 6, 2017

(65) Prior Publication Data

US 2018/0100205 A1   Apr. 12, 2018

Related U.S. Application Data

(60) Provisional application No. 62/406,166, filed on Oct. 10, 2016.

(51) Int. Cl.
*C12Q 1/70* (2006.01)
*C12Q 1/6851* (2018.01)

(52) U.S. Cl.
CPC ........... *C12Q 1/703* (2013.01); *C12Q 1/6851* (2013.01); *C12Q 1/705* (2013.01); *C12Q 1/706* (2013.01); *C12Q 1/707* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,130,238 A | 7/1992 | Malek et al. | |
| 5,677,124 A | 10/1997 | DuBois et al. | |
| 5,919,625 A | 7/1999 | DuBois et al. | |
| 5,939,262 A | 8/1999 | Pasloske et al. | |
| 6,440,725 B1 | 8/2002 | Pourahmadi et al. | |
| 6,783,934 B1 | 8/2004 | McMillan et al. | |
| 6,818,185 B1 | 11/2004 | Petersen et al. | |
| 6,979,424 B2 | 12/2005 | Northrup et al. | |
| 7,718,421 B2 | 5/2010 | Chen et al. | |
| 8,580,559 B2 | 11/2013 | Petersen et al. | |
| 8,609,340 B2 | 12/2013 | Eickhoff et al. | |
| 8,940,526 B2 | 1/2015 | Ririe et al. | |
| 9,322,052 B2 | 4/2016 | Petersen et al. | |
| 2010/0005638 A1 | 1/2010 | Fujii | |
| 2011/0142863 A1 | 6/2011 | Iyer et al. | |

FOREIGN PATENT DOCUMENTS

| | | |
|---|---|---|
| EP | 0439182 | 7/1991 |
| WO | WO 90/01069 | 2/1990 |
| WO | WO 92/08808 | 5/1992 |
| WO | WO2010036391 | 4/2010 |
| WO | WO2012013734 | 2/2012 |

OTHER PUBLICATIONS

Whelen A. C. and Persing D. H., Annu. Rev. Microbiol. 50(1996) 349-373.
Barany F., Proc. Natl. Acad. Sci. USA 88 (1991)189-193.
Baraby F., PCR Methods and Applic. 1 (1991) 5-16.
Kwoh D.Y. et al., Proc. Natl. Acad. Sci. USA 86 (1989) 1173-1177.
Guatelli J.C., et al., Proc. Natl. Acad. Sci. USA 87 (1990) 1874-1878.
Verreault, et al., "Resistance of Aerosolized Bacterial Viruses to Relative Humidity and Temperature," Applied & Environmental Microbiology, vol. 81, No. 20, Aug. 7, 2015, 7305-7311.
International Search Report dated Jan. 11, 2018 for International App. No. PCT/EP2017/075725.

*Primary Examiner* — Nicole Kinsey White
(74) *Attorney, Agent, or Firm* — Pamela C. Ancona

(57) ABSTRACT

The disclosure provides control compositions used in nucleic acid amplification. Various modifications to the disclosed compositions and methods of using the same, devices, and kits are described.

15 Claims, 5 Drawing Sheets

Specification includes a Sequence Listing.

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tgcgatccgt gtccaagggt tcgc                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcatttctgg agcagtgcat                                               20

```
<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gactgccaag gtgccatta                                                   19
```

DEVICES COMPRISING BACTERIOPHAGE PHI6 INTERNAL CONTROL COMPOSITIONS

CROSS-REFERENCE TO RELATED APPLICATION

The present application claims the benefit of priority of U.S. Provisional Application Ser. No. 62/406,166, filed Oct. 10, 2016, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 11, 2017, is named P33787-US_SL.txt and is 938 bytes in size.

FIELD OF THE INVENTION

Compositions including Phi6 bacteriophage are disclosed for use in nucleic acid amplification methods. Also disclosed are sample processing devices and kits configured to perform nucleic acid amplification methods wherein the devices and/or kits include a Phi6 internal control composition.

BACKGROUND OF THE INVENTION

Various methods have been developed for the amplification of nucleic acids, including Polymerase Chain Reaction (PCR), Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification. Each of these methods involves a series of complex and sensitive steps and an accurate, qualitative and/or quantitative assay requires that variability at each step is carefully controlled. It is also critical that the control standards are precisely calibrated and they can withstand the rigors of the assay procedures.

Qualitative detection of a nucleic acid in a biological sample is crucial, e.g. for recognizing an infection of an individual, and therefore false-negative and false-positive results should be minimized. Thus, a qualitative internal control nucleic acid is added to the detection mix. Moreover, quantifying viral nucleic acid sequences in a biological sample is an important tool for assessing a patient's viral load, i.e., the measure of the total quantity of viral particles within a given patient at one point in time. In chronic infections, viral load is a function of a highly dynamic equilibrium of viral replication and immune-mediated host clearance. Viral load can be used to assess the degree of viral replication at the time of diagnosis which provides an assessment of the patient's progression and prognosis. It can also be used to monitor the effect of antiviral medications early in the disease course and quickly assess the effects of changing antiviral medications.

Numerous nucleic acids relevant for clinical diagnostics are ribonucleic acids, e.g. the nucleic acids from RNA viruses such as, for example, Human Immunodeficiency Virus (HIV), Hepatitis C Virus (HCV), West Nile Virus (WNV), Human Papilloma Virus (HPV), Japanese Encephalitis Virus (JEV), St. Louis Encephalitis Virus (SLEV), Influenza Virus, Norovirus, and others. Therefore, it can be advantageous to use an internal control nucleic acid consisting of RNA in order to reflect the properties of the target nucleic acids in the sample. Because RNA is more prone to degradation than DNA due to its inherent sensitivity to influences such as alkaline pH, ribonucleases, etc., internal control nucleic acids made of RNA are commonly provided as armored particles. Armored RNA® (aRNA) technologies stabilize and protect nucleic acids from nuclease degradation by packaging them in a protective bacteriophage protein coat. (Armored RNA is developed by Ambion, Inc. and Cenetron Diagnostics LLC, both of Austin, Tex., and covered under U.S. Pat. Nos. 5,677,124, 5,919,625 and 5,939,262, the disclosures of which are incorporated herein by reference in their entireties.) These aRNA constructs are fully processed within the assay, they are thermostable at ambient temperatures, and they are relatively RNase resistant. However, at high temperatures, aRNA constructs rapidly degrade, resulting in assay loss. In order to extend the shelf life of products including these constructs, the products are shipped and stored at 4° C., which is costly. Therefore, there is a need for a heat resistant, ribonuclease-resistant RNA standard for use in qualitative and/or quantitative nucleic acid detection methods.

SUMMARY OF THE INVENTION

Disclosed and claimed are heat-resistant, ribonuclease-resistant RNA standard formulations for use in qualitative and/or quantitative nucleic acid detection methods. The compositions described herein are thermostable for up to 110 days at 30° C., and particularly up to 28 days at 45° C.

Therefore, the disclosure provides a composition comprising a Phi6 bacteriophage suspended in a buffer suitable for a nucleic acid amplification reaction at a pH between 7-9, including a chelating agent and a preservative, and optionally comprising one or more additional components selected from BSA, gelatin, poly rA RNA, glycerol, amino acids, trehalose, casein, or polyethylene glycol.

Also provided is a device configured to perform a viral load analysis in a sample, wherein the device includes a sample introduction port adapted to receive a sample aliquot; an internal control compartment comprising a composition as described herein; and a PCR analysis region comprising one or more additional compartments each configured to conduct one or more steps of a PCR analysis comprising reagent preparation, target enrichment, inhibitor removal, nucleic acid extraction, amplification, and real-time detection.

DETAILED DESCRIPTION

Definitions

Figure 1:
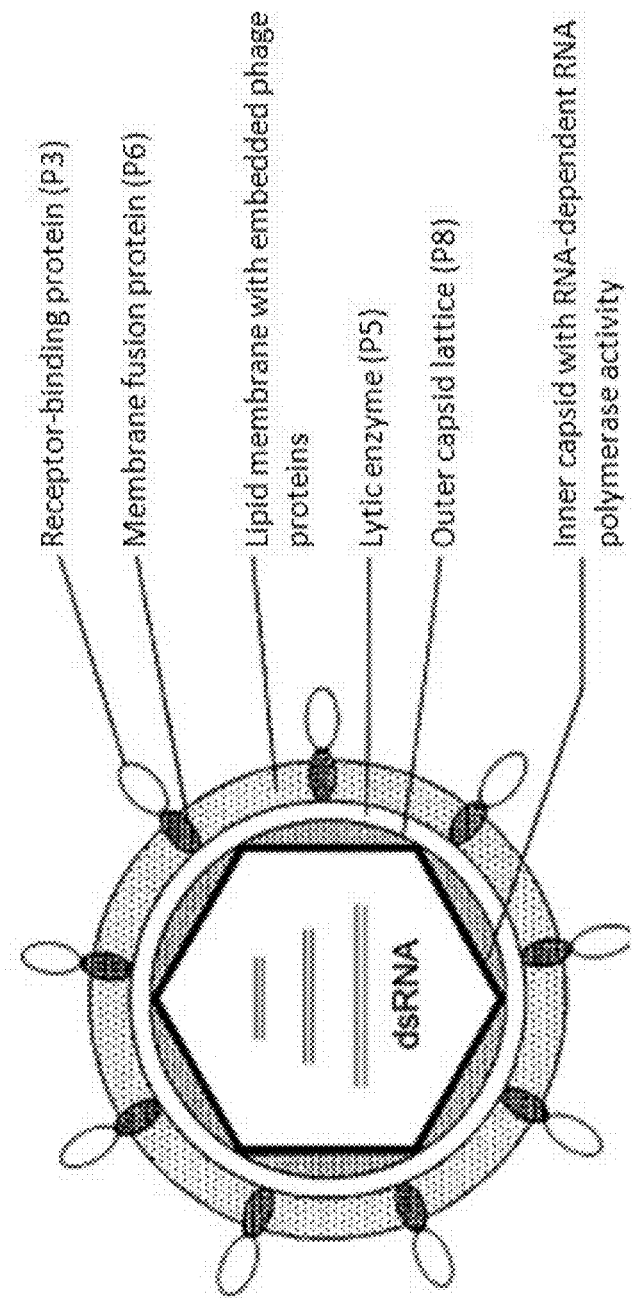
FIG. 1 shows the structure of the Phi6 bacteriophage.

Unless otherwise defined herein, scientific and technical terms used herein have the meanings that are commonly understood by those of ordinary skill in the art. Further, unless otherwise required by context, singular terms include pluralities and plural terms include the singular. The articles "a" and "an" are used herein to refer to one or to more than one (i.e., to at least one) of the grammatical object of the article. By way of example, "an element" means one element or more than one element.

The terms "detect," "detecting," "detection," and similar terms are used in this application to broadly refer to a process or discovering or determining the presence or an absence, as well as a degree, quantity, or level, or probability of occurrence of something. For example, the term "detecting" when used in reference to a target nucleic acid sequence, can denote discovery or determination of the presence, absence, level or quantity, as well as a probability or likelihood of the presence or absence of the sequence. It is to be understood that the expressions "detecting presence or absence," "detection of presence or absence" and related expressions include qualitative and quantitative detection.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

One method of nucleic acid amplification is the Polymerase Chain Reaction (PCR) which is disclosed in U.S. Pat. Nos. 4,683,202, 4,683,195, 4,800,159, and 4,965,188, among other references. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have, for example, been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec to 9 min. In order to not expose the respective polymerase to such high temperatures for too long and thus risking a loss of functional enzyme, it is preferred to use short denaturation steps. In a specific embodiment, the denaturation step is up to 30 sec, e.g., up to 20 sec, up to 10 sec, up to 5 sec, and specifically, about 5 sec.

If the double-stranded template nucleic acid is denatured by heat, the reaction mixture is allowed to cool to a temperature that promotes annealing of each primer to its target sequence on the target nucleic acids. The temperature for annealing is preferably from about 35° C. to about 70° C., further preferably about 45° C. to about 65° C.; further preferably about 50° C. to about 60° C., further preferably about 55° C. to about 58° C. Annealing times can be from about 10 sec to about 1 min (e.g., about 20 sec to about 50 sec; about 30 sec to about 40 sec). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since at higher temperatures the probability of primer binding to not exactly matching target sequences continuously decreases. In order to benefit from both phenomena, in some embodiments of the invention it is preferred that the process described above comprises annealing at different temperatures, preferably first at a lower, then at a higher temperature. If, e.g., a first incubation takes place at 55° C. for about 5 cycles, non-exactly matching target sequences may be (pre-) amplified. This can be followed e.g. by about 45 cycles at 58° C., providing for higher specificity throughout the major part of the experiment. This way, potentially important genetic variants are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 sec to about 5 min, preferably about 15 sec to 2 min, further preferably about 20 sec to about 1 min, further preferably about 25 sec to about 35 sec. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

A PCR assay can be carried out in which the steps of annealing and extension are performed in the same step (one-step PCR) or, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, a one-step PCR reduces the overall complexity of the respective assay.

In general, shorter times for the overall amplification are preferred, as the time-to-result is reduced and leads to a possible earlier diagnosis.

Other preferred nucleic acid amplification methods that may include the use of the standards described herein include, but are not limited to, the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, the standards described herein can also be used in the following methods: strand displacement amplification (SDA), transcription mediated amplification (TMA), and Qb-amplification (for a review see e.g. Whelen A. C. and Persing D. H., Annu. Rev. Microbiol. 50 (1996) 349-373; Abramson R. D. and Myers T. W., Curr Opin Biotechnol 4 (1993) 41-47).

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence. This region of is typically about 15 to about 40 nucleotides in length. A "primer pair" refers to a forward primer and reverse primer (sometimes called 5' and 3' primers) that are complementary to opposite strands of a target sequence and designed to amplify the target sequence. The forward and reverse primers are arranged within an amplifiable distance of each other on the target sequence, e.g., about 10-5000 nucleotides, or about 25-500 nucleotides.

As used herein, "probe" means any molecule that is capable of selectively binding to a specifically intended target biomolecule, for example, a nucleic acid sequence of interest to be bound, captured or hybridized by the probe.

The words "complementary" or "complementarity" refer to the ability of a nucleic acid in a polynucleotide to form a base pair with another nucleic acid in a second polynucleotide. For example, the sequence 5'-A-G-T-3' (5'-A-G-U-3' for RNA) is complementary to the sequence 3'-T-C-A-5' (3'-U-C-A-5' for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The term "amplification conditions" or similar expressions refer to conditions in a nucleic acid amplification reaction (e.g., PCR amplification) that allow for hybridization and template-dependent extension of the primers, as described herein above. The term "amplicon" refers to a nucleic acid molecule that contains all or a fragment of the target nucleic acid sequence and that is formed as the product of in vitro amplification by any suitable amplification method. Various PCR conditions are described in PCR Strategies (Innis et al., 1995, Academic Press, San Diego, Calif.) at Chapter 14; PCR Protocols: A Guide to Methods and Applications (Innis et al., Academic Press, N Y, 1990).

The term "sample" or "biological sample" refers to any composition containing or presumed to contain nucleic acid from an individual. The term includes purified or separated components of cells, tissues, or blood, e.g., DNA, RNA, proteins, cell-free portions, or cell lysates. In one embodiment, the sample is a whole blood sample. As used herein, a "whole blood sample" includes blood drawn from the body from which no constituent, such as plasma or platelets, has been removed. Generally, the sample is unmodified except for the presence of an anticoagulant. A sample can also refer to other types of biological samples, e.g., plasma, serum, blood components (buffy coat), and dried blood spots. Samples also may include constituents and components of in vitro cultures of cells obtained from an individual, including cell lines. Specific additional examples of biological samples include feces, mucosal swabs, tissue aspirates, tissue homogenates, cell cultures and cell culture supernatants (including cultures of eukaryotic and prokaryotic cells), urine, saliva, sputum, and cerebrospinal sample.

The internal control compositions described herein can serve as a "quantitative standard nucleic acid" which is a reference used to determine the quantity of the target nucleic acids. For this purpose, quantitative standard nucleic acids undergo all possible sample preparation steps along with the target nucleic acids. Moreover, a quantitative standard nucleic acid is processed throughout the assay method within the same reaction mixture. It must generate, directly or indirectly, a detectable signal both in the presence or absence of the target nucleic acid. For this purpose, the concentration of the quantitative standard nucleic acid has to be optimized in each test in order not to interfere with sensitivity but in order to generate a detectable signal also e.g. at very high target concentrations. In terms of the limit of detection (LOD, see below) of the respective assay, the concentration range for the "quantitative standard nucleic acid" is 20-5000×LOD, particularly 20-1000×LOD, and specifically 20-5000×LOD. The final concentration of the quantitative standard nucleic acid in the reaction mixture is dependent on the quantitative measuring range accomplished.

"Limit of detection" or "LOD" means the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard.

A composition is "thermostable" if it is capable of withstanding moderate heat, e.g., temperatures between 37-60° C. for up to 200 days without a significant loss in cycle threshold (Ct). In real-time PCR, a positive reaction is detected by the accumulation of a fluorescent signal and the Ct value is defined as the number of cycles required for the fluorescent signal to cross the threshold at which point the signal exceeds the background level. Ct is inversely proportional to the amount of target nucleic acid in the sample. The ΔCt corresponds to the difference between the Ct of a sequence of interest and the Ct of the internal control. In one embodiment, the ΔCt for an internal control composition as described herein is <1-3 at 45° C. for up to 28 days, and more specifically, the ΔCt is <1 at 45° C. for up to 28 days. Moreover, the compositions described herein are thermostable following one or more freeze-thaw cycles from −80° C. to 4° C.

Compositions

Bacteriophage Φ6 (Phi 6) is an enveloped double stranded RNA virus with a segmented genome. Unlike single stranded RNA genomes, such as aRNA, Phi6 has two protective armored layers: a protein capsid and a lipid membrane. This is illustrated in FIG. 1.

Phi6 can be formulated in any medium suitable for use in a nucleic acid amplification assay. In one embodiment, up to approximately 4e5 copies/mL of lyophilized Phi6 is suspended in a suitable buffer, e.g., a citrate-based, glycine-based, tricine-based buffer, as well as PIPES, and HEPES, at a pH of 7-9. For nucleic acid amplification methods, a phosphate-based buffer should be avoided. In a specific embodiment, the buffer is Tris-HCl, e.g., at a concentration of 5-20 mM, specifically 8-12.5 mM, and particularly, 10 mM, and a pH of 7-9, and specifically pH 8.

The formulation can also include a chelating agent, e.g., EDTA or EGTA, and a preservative, e.g., $NaN_3$ or Pro-Clin300. In a specific embodiment, the formulation includes EDTA and $NaN_3$. In one embodiment, the chelating agent is 0.01-1.0 mM EDTA, e.g., 0.1 mM EDTA and the preservative is 0.01-1.0 mM sodium azide, e.g., 0.05% $NaN_3$.

One or more additional components can be included in the formulation, including but not limited to 0-25 mg/mL bovine serum albumin (BSA), 0-3% gelatin, 0-100 mg/L poly RNA, 0-40% glycerol, 0-25 mg/mL amino acids, e.g., glutamine, etc., trehalose, casein, 5-40% polyethylene glycol (PEG), etc.

In a specific embodiment, a stock of internal control can include between 1000 and 1,000,000 copies/mL of lyophilized Phi6, and more specifically, between 100,000 and 750,000 copies.

Table 1 provides a non-limiting set of examples of suitable Phi6 formulations:

TABLE 1

| Example | Composition |
|---|---|
| (a) | up to ~4e5 cp/mL of lyophilized Phi6 in 10 mM Tris, pH 8.0 |
| | 0.1 mM EDTA |
| | 0.05% Sodium Azide |
| | 25 mg/mL BSA |
| (b) | up to ~4e5 cp/mL of lyophilized Phi6 in 10 mM Tris, pH 8.0 |
| | 0.1 mM EDTA |
| | 0.05% Sodium Azide |
| | 1% gelatin |
| (c) | up to ~4e5 cp/mL of lyophilized Phi6 in 10 mM Tris, pH 8.0 |
| | 0.1 mM EDTA |
| | 0.05% Sodium Azide |
| | 20 mg/L poly rA RNA |
| (d) | up to ~4e5 cp/mL of fresh cultured Phi6 in 10 mM Tris, pH 8.0 |
| | 0.1 mM EDTA |
| | 0.05% Sodium Azide |
| | 20 mg/L poly rA RNA |
| | 40% glycerol |
| (e) | up to ~4e5 cp/mL of lyophilized Phi6 in 10 mM Tris, pH 8.0 |
| | 0.1 mM EDTA |
| | 0.05% Sodium Azide |
| | 20 mg/L poly rA RNA |
| | 40% glycerol |
| (f) | up to ~4e5 cp/mL of lyophilized Phi6 in 0.1M NaCl |
| | 8 mM $MgSO_4$ |
| | 0.05M Tris-HCl, pH 7.5 |
| | 0.01% (wt/vol) solid gelatin |

Phi6 compositions are stable at 45° C. for up to 28 days, at 50° C. for up to 14 days, and at 30° C. for up 110 days. In addition, the formulations are tolerant of one or more freeze-thaw cycles, e.g., between −80° C. to 4° C.

Assay Systems & Sample Processing Devices

The control materials described herein can be used in any manual amplification assay method or in an automated nucleic acid amplification system or sample preparation system. In one embodiment, the control materials can be used in any suitable commercially available PCR instrumentation and/or sample preparation system, including but not limited to, the Cobas® 6800/8800 System, Cobas® 4800 System, the Cobas® AmpliPrep Instrument, the Cobas® LIAT® System, the Cobas® p630 Instrument, the Cobas® s201 System, the Cobas® TaqMan® 48 Analyzer, the Cobas® TaqMan® Analyzer, the LightCycler® 1536 System, the LightCycler® 2.0 System, the LightCycler® 480 System, the LightCycler® 96 System, the MagNA Pure 96 System, the MagNA Pure Compact System, the MagNA Pure LC 2.0 System, or the FLOW Solution (see., e.g., www.molecular.roche.com/systems).

In a specific embodiment, the compositions described herein are used in a sample processing device configured to perform a nucleic acid amplification technique. Nucleic acids extracted from a biological sample may be further processed by amplifying the nucleic acids using any of the methods described hereinabove. In a specific embodiment, the nucleic acids extracted from the organism are RNA and their processing includes a coupled reverse transcription and polymerase chain reaction (RT-PCR) using combinations of enzymes such as Tth polymerase and Taq polymerase or reverse transcriptase and Taq polymerase. In some embodiments, nicked circular nucleic acid probes can be circularized using T4 DNA ligase or Amphgase™ and guide nucleic acids, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TaqMan™, molecular Beacons™, fluorescence resonance energy transfer (FRET) probes, Scorpion™ probes) and generally use fluorescence quenching as well as the release of quenching or fluorescence energy transfer from one reporter to another to detect the synthesis or presence of specific nucleic acids.

In one embodiment, the compositions disclosed herein are used in a device comprising self-contained microscale to macroscale channels, chambers, reservoirs, detection and processing regions. The device can be a cartridge, device, container, or pouch, e.g., as described in U.S. Pat. Nos. 6,440,725; 6,783,934; 6,818,185; 6,979,424; 8,580,559; and 8,940,526, the disclosures of which are incorporated herein by reference in their entireties, as well as devices such as those available from Cepheid Corp., Idaho Technology, Inc., and/or Biofire Diagnostics, Inc.

For example, the device can be a self-contained nucleic acid analysis pouch which includes a cell lysis zone, a nucleic acid preparation zone, a first-stage amplification zone, a second-stage amplification zone, as shown in FIG. 1 of US Application Publication No. 201000056383, the disclosure of which is incorporated herein by reference. The pouch comprises a variety of channels and blisters of various sizes and is arranged such that the sample flows through the system and various zones and processed accordingly. Sample processing occurs in various blisters located within the pouch. Numerous channels are provided to move the sample within and between processing zones, while other channels are provided to deliver fluids and reagents to the sample or to remove such fluids and reagents from the sample. Liquid within the pouch is moved between blisters by pressure, e.g., pneumatic pressure. In this particular embodiment, the compositions described herein are provided in an internal control compartment configured to house the composition and in fluid communication with one or other channels and blisters such that the composition can be incorporated into the sample processing workflow and processed accordingly.

In an alternative example, the device can be a self-contained nucleic acid analysis cartridge as shown in FIGS. 3-5 and 9 of U.S. Pat. No. 9,322,052, which is incorporated herein by reference. The cartridge includes, inter alia, multiple chambers comprising a sample chamber for holding a fluid sample introduced through the inlet port, a wash chamber for holding a wash solution, a reagent chamber for holding a lysing reagent, a lysis chamber, a waste chamber for receiving used sample and wash solution, a neutralizer chamber for holding a neutralizer, and a master mix chamber for holding a master mix (e.g., amplification reagents and fluorescent probes) and for mixing the reagents and probes with analyte separated from the fluid sample, a reaction vessel, and a detection chamber. In this embodiment, the compositions described herein are provided in an internal control compartment configured to house the composition and in fluid communication with one or other channels and blisters such that the composition can be incorporated into the sample processing workflow and processed accordingly.

In a specific embodiment, the methods described herein are conducted in a sample processing device such as that described in U.S. Pat. No. 7,718,421, the disclosure of which is incorporated herein by reference. Segmented devices, such as those described in U.S. Pat. No. 7,718,421, provide a convenient vessel for receiving, storing, processing, and/or analyzing a biological sample. In certain embodiments, the segmented device facilitates sample processing protocols involving multiple processing steps. In certain embodiments, a sample may be collected in a sample device, and the device is then positioned in an analyzer which manipulates the device and its contents to process the sample.

A particular embodiment includes a flexible device which has been segmented into compartments by breakable seals. The individual segments may contain various reagents and buffers for processing a sample. Clamps and actuators may be applied to the device in various combinations and with various timings to direct the movement of fluid and to cause the breakable seals to burst. This bursting of the breakable seals may leave an inner device surface that is substantially free of obstructions to fluid flow. In one embodiment, the flow of the biological sample may be directed toward the distal end of the device as the processing progresses, while the flow of waste may be forced to move in the opposite direction, toward the opening of the device where the sample was initially input. This sample inlet can be sealed, possibly permanently, by a cap with a locking mechanism, and a waste chamber may be located in the cap to receive the waste for storage. A significant benefit of this approach is that the processed sample does not come into contact with surfaces that have been touched by the unprocessed sample. Consequently, trace amounts of reaction inhibitors present in the unprocessed sample that might coat the walls of the device are less likely to contaminate the processed sample.

Figure 2:
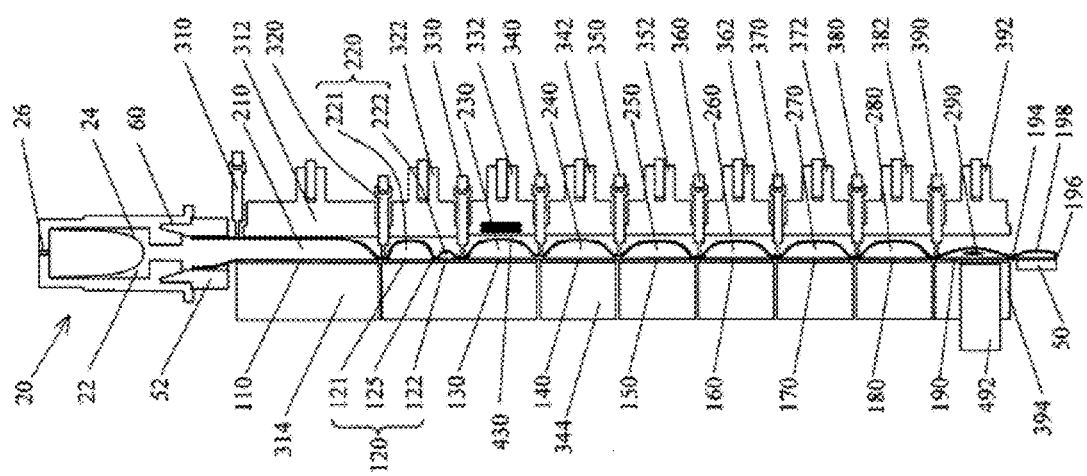
FIG. 2 shows a sample processing device that can be used with the compositions described herein.

The sample processing device is shown in FIG. 2 and may include a transparent flexible device 10 capable of being configured into a plurality of segments, such as 16, 110, 120, 130, 140, 150, 160, 170, 180, and/or 190, and being substantially flattened by compression. In an embodiment, a device may have at least two segments. In an embodiment, a device may have at least three segments. The flexible device can provide operational functionality between approximately 2-105° C., compatibility with samples, targets and reagents, low gas permeability, minimal fluorescence properties, and/or resilience during repeated compression and flexure cycles. The device may be made of a variety of materials, examples of which include but are not limited to: polyolefins such as polypropylene or polyethylene, polyurethane, polyolefin co-polymers and/or other materials providing suitable characteristics.

In exemplary embodiments, one or more reagents can be stored either as dry substance and/or as liquid solutions in device segments. In embodiments where reagents may be stored in dry format, liquid solutions can be stored in adjoining segments to facilitate the reconstitution of the reagent solution. Examples of typical reagents include: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, and phosphothioate nucleic acid probes. In embodiments where one of the reagents is a chaotropic salt solution, a preferred component is guanidinium isocyanate or guanidinium hydrochloride or a combination thereof. In some embodiments, the order in which reagents may be stored in the device relative to the opening through which a sample is input, reflects the order in which the reagents can be used in methods utilizing the tube. In preferred embodiments, a reagent includes a substance capable of specific binding to a preselected component of a sample. For example, a substance may specifically bind to nucleic acid, or a nucleic acid probe may specifically bind to nucleic acids having particular base sequences.

A real-time detection of a signal from a device segment can be achieved by using a sensor 492 (FIG. 2), such as a photometer, a spectrometer, a CCD, connected to a block, such as block 490. In exemplary embodiments, pressure can be applied by an actuator 392 on the device segment 190 to suitably define the device segment's shape. The format of signal can be an intensity of a light at certain wavelength, such as a fluorescent light, a spectrum, and/or an image, such as image of cells or manmade elements such as quantum dots. For fluorescence detection, an excitation of light from the optical system can be used to illuminate a reaction, and emission light can be detected by the photometer. To detect a plurality of signals having specific wavelengths, different wavelength signals can be detected in series or parallel by dedicated detection channels or a spectrometer.

Kits

In some embodiments, the compositions described herein are included in a kit or a component thereof. The kits contemplated herein can include any manufacture (e.g., a package or a container), including at least one device for specifically amplifying, capturing, tagging/converting or detecting a target nucleic acid sequence as described herein, wherein the compositions described herein are included in the device or provided as a separate kit component, vial or container. The kit can further include instructions for use, supplemental reagents, control materials, and/or components or modules used in the amplification methods described herein or a step thereof. One or more of the kit components can be included in the kit as separate components, e.g., in separate vials or containers packaged together, or one or more of the kit components can be included in the kit in the same vial or container.

Such kits may comprise components which can be used during a sample preparation procedure, e.g., microtiter plates in the 96- or 384-well format or ordinary reaction tubes manufactured, e.g., by Eppendorf, Hamburg, Germany and all other reagents for carrying out a nucleic acid amplification using the control materials described herein. The kit can also include a solid support having an affinity for nucleic acids, e.g., a material with a silica surface. In one embodiment, the solid support comprises, e.g., magnetic glass particles. The kit can further or additionally comprise a protease reagent and a lysis buffer containing e.g. chaotropic agents, detergents or alcohols or mixtures thereof allowing for the lysis of cells. These components of the kit may be provided separately in tubes or storage containers. Depending on the nature of the components, these may be provided in a single tube or storage container.

The kit may further or additionally comprise a washing solution which is suitable for the washing step of the magnetic glass particles when a nucleic acid is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use.

The kit may further comprise an eluent or elution buffer, i.e. a solution or a buffer (e.g. 10 mM Tris, 1 mM EDTA, pH 8.0) or pure water to elute the nucleic acid bound to the magnetic glass particles. Further, additional reagents or buffered solutions may be present which can be used for the purification of a nucleic acid.

In a specific embodiment, the kit contains a polymerase enzyme having 5' to 3' exonuclease activity. The kit can also contain an enzyme with reverse transcriptase activity. In another embodiment, the kit contains a polymerase enzyme having 5' to 3' exonuclease activity and reverse transcriptase activity.

Methods & Uses

The compositions described herein can be used to analyze any viral pathogen, including but not limited to Human Immunodeficiency Virus (HIV), Hepatitis C Virus (HCV), the West Nile Virus (WNV), Human Papilloma Virus (HPV), Japanese Encephalitis Virus (JEV), St. Louis Encephalitis Virus (SLEV), Influenza Virus, Norovirus, and others. The compositions can also be used to detect other forms of RNA, e.g., mRNA or miRNA from non-viral organisms (e.g., human, bacteria, etc.). In a specific embodiment, the compositions can be used to detect any pathogenic strain of HIV, including HIV-1 and HIV-2, and any group or subtype thereof, as well as hepatitis or cytomegalovirus. For example, the compositions can be used an assay method to analyze HIV-1 group(s) M, N, O, P, and combinations thereof. In a specific example, the compositions are used to analyze HIV-1 group M and/or O, and optionally one or more additional HIV-1 groups. The compositions can also be used to analyze one or more subtypes of HIV-1, including but not limited to subtypes, A, A1, A2, CRF19, B, C, D, F, G, CRF02_AG, H, CRF04_cpx, J, K, and combinations thereof. In addition, the methods can also be used to detect HIV-2, groups A-H, and in particular, HIV-2 groups A and B. In addition, hepatitis can also be analyzed using the compositions described herein, including but not limited to, hepatitis A, B or C, and in particular, hepatitis B or C can be analyzed using the compositions described herein.

EXAMPLES

Example 1. Viral RNA Isolation and Detection from Whole Blood in a Sample Processing Device RNA isolation and RNA sequence detection can be accomplished in a tube 1 (FIG. 2), including a flexible device having nine segments separated by peelable seals and containing pre-packed reagents, and a cap, having a waste reservoir housed therein. Fluid flow from one segment or subsection of the device to another is controlled as described herein by selective engagement of one or more actuators and clamps operably connected within one or more segments or subsections of the device. The first segment of the device can receive the whole blood sample. The additional segments of the device comprise the following components in the following order:

TABLE 2

| Segment | Component |
| --- | --- |
| 2 | Phi6 control formulation (up to ~4e5 cp/mL of fresh cultured Phi6 in 10 mM Tris, pH 8.0, 0.1 mM EDTA, 0.05% Sodium Azide, 20 mg/L poly rA RNA, 40% glycerol) |

TABLE 2-continued

| Segment | Component |
|---|---|
| 3 (two subsections separated by a peelable seal) | Subsection 1: 200 ug proteinase K<br>Subsection 2: 250 ug Silica Magnetic particles |
| 4 | 200 ul of lysis buffer comprising chaotropic salts which contain 4.7M guanidinium hydrochloride, 10 mM urea, 10 mM Tris HCl, pH 5.7, and 2% triton X-100 |
| 5 | 80 ul of wash buffer (including, e.g., 50% ethanol, 20 mM NaCl, 10 mM Tris HCl, pH 7.5). |
| 6 | 80 ul of 20 mM 2-morpholinoethanesulfonic acid (MES) buffer, pH 5.3. (pH adjusted to be low enough to avoid DNA elution from the particles) |
| 7 | 40 ul elution buffer (e.g., 10 mM Tris HCl, pH 8.5, or any buffer suitable for PCR; elution buffer pH adjusted to be high enough to elute the DNA from the surface of the particles into the buffer) |
| 8 | PCR reagents (which can contain 10 nmol of each one of: dATP, dCTP, and dGTP; 20 nmol dUTP, 2.5 mmol of KCl, 200 nmol of $MgCl_2$, 1-5 units of Taq DNA polymerase, 1-5 units of Tth DNA polymerase, 20-100 pmol of each of the oligonucleotide primers, and 6-25 pmol of TaqMan probe) |
| 9 | Divalent metal cofactor, such as $MgCl_2$ |

For viral RNA isolation and detection, 100 ul of whole blood is loaded into the $1^{st}$ segment. The device can then be closed by a cap and inserted into a Cobas® LIAT® Analyzer (available from Roche Molecular Systems, Pleasanton, Calif.). Sample processing can include the following steps.

(1) Sample Lysis. All clamps, except the first clamp, are closed on the device. The actuator operably connected with the $1^{st}$ segment is used to adjust the volume of blood to retain about 100 ul in the segment, and then the $1^{st}$ segment is closed using the associated segment clamp. The actuator operably connected with the $2^{nd}$ segment, in whole or in part, compresses the first subsection of the $2^{nd}$ segment to break the peelable seal and mix the control material with the sample. Actuators operably connected with the first subsection can alternately compress the subsection to mix the control with the sample. By engaging the associated actuators and clamps in that segment/subsection, the sample is moved to the $3^{rd}$ segment, a clamp is closed above the $3^{rd}$ segment to prevent the sample from mixing with the downstream specimen, and then moved to the $4^{th}$ segment to mix the lysis buffer with the sample. The mixture in the $3^{rd}$ and $4^{th}$ segments is incubated at 50° C. for 2 minutes.

(2) Nucleic Acid Capture. After lysis incubation, the actuators alternately compress their respective segments to agitate and incubate the mixture for 2 minutes at room temperature to facilitate DNA binding to the particles. Then, a magnetic field is generated by a magnetic source near the segment to capture the particles in suspension. The actuators can alternately compress the segment to capture the particles. The actuators and clamps are sequentially opened and closed to move the unbound sample and waste to the waste reservoir.

(3) Wash. A wash process follows the capture process in order to remove residual debris and reaction inhibitors from the particles and the segments that would be used for further sample processing. A dilution-based washing is used with the ethanol wash buffer and a thin-layer flow-based washing is used with the MES wash buffer. Clamps and actuator first open, and then the actuator closes to move the ethanol buffer to the $5^{th}$ segment, followed by the closing of the clamp. The magnetic field is removed; the actuator and at least one adjacent actuator is alternately compressed against their respective segments to generate flow to re-suspend the particles. The magnetic field is then turned on to capture substantially all the particles and the liquid is moved to a waste reservoir. After completing the first wash, the MES wash buffer is moved from one segment to another and the buffer is manipulated using the sequential application and release of the corresponding actuators and clamps to ensure an essentially laminar flow of the wash buffer through the flow channel. When the wash is completed, the actuators and clamps are closed and substantially all the waste is moved to the waste reservoir.

(4) Nucleic Acid Elution. The elution buffer is moved from the $7^{th}$ segment using a similar process as mentioned before. The magnetic field can be removed and the particles are re-suspended in the elution buffer under flow between the fourth and fifth segments. The particle suspension is incubated at 95° C. under stationary flow or agitation conditions for 2 minutes. The magnetic field is turned on and substantially all the particles are immobilized, and the eluted nucleic acid solution can be moved to the $7^{th}$ segment by sequentially opening and closing the actuators and clamps. The actuators can compress the $7^{th}$ segment to adjust the volume of the eluted nucleic acid solution to 40 ul and a clamp can then close against the device to complete the DNA extraction process.

(5) Nucleic Acid Amplification and Detection. The nucleic acid solution can then be transferred to the $8^{th}$ segment, mixed, and incubated with UNG 280 at 37° C. for 1 minute to degrade any contaminant PCR products that may have been present in the biological sample. After the incubation, the temperature may be increased to 95° C. to denature nucleic acids and UNG for 2 minutes. The nucleic acid solution can then be transferred to the $9^{th}$ segment, and mixed with RT-PCR reagents at 65° C. for 10 minutes, followed by incubation at 60° C. to initiate hot start PCR. A typical 2-temperature, amplification assay of 50 cycles of 95° C. for 2 seconds and 60° C. for 15 seconds can be conducted by setting the $8^{th}$ segment at 95° C. and the $9^{th}$ segment at 60° C., and transferring the reaction mixture between the segments alternately by closing and opening the associated actuators. A typical 3-temperature, amplification assay of 50 cycles of 95° C. for 2 seconds, 60° C. for 10 seconds, and 72° C. for 10 seconds can be conducted by setting the $7^{th}$ segment at 95° C., $8^{th}$ segment at 72° C. and the $9^{th}$ segment at 60° C., and alternately transferring the reaction mixture among the segments by closing and opening the associated actuators. A detection sensor, such as a photometer, optically connected to the 9$^{th}$ chamber can monitor real-time fluorescence emission from the reporter dye through a portion of the device wall. After an assay is complete, the test results are reported.

Example 2. Viral RNA Isolation and Detection in a Sample Using a LightCycler 480

A sample of HIV-1M (50000 cp/mL, Roche) are analyzed using a LightCycler 480 (Roche Molecular Systems). For sample preparation, the following reagents are used as diluents: ReservCyt (available from Thin Prep) and K3 EDTA Plasma, PCR neg. (available from Roche). The sample is diluted to a final concentration of 100 cp/ML in K3 EDTA Plasma and stored overnight (plasma dilutions at −60 to −90° C., PreservCyt dilutions at 2-8° C.).

The sample (500 ul) and diluent (350 ul) are pipetted manually into a deepwell plate, and separate aliquots of sample are added to three different wells for triplicate analysis. A 50 uL aliquot of an internal control nucleic acid (Phi6 control formulation: up to −4e5 cp/mL of fresh cultured Phi6 in 10 mM Tris, pH 8.0, 0.1 mM EDTA, 0.05% Sodium Azide, 20 mg/L poly rA RNA, 40% glycerol) is manually added. Sample preparation is performed on a Hamilton Star (Hamilton, Bonaduz, CH), following the workflow according to the scheme depicted in FIG. 1 of U.S. Pat. No. 8,609,340 (the disclosure of which is incorporated herein by reference in its entirety) using the following reagents:

TABLE 3

|  | Conc. or pH |
|---|---|
| Protease reagent | |
| Tris (mM) | 10 |
| EDTA (mM) | 1 |
| Calcium Chloride (mM) | 5 |
| Calcium Acetate (mM) | 5 |
| Esperase (mg/ml) | 80 |
| Glycerin (w/v, %) | 50 |
| pH | 5.5 |
| MGP Reagent | |
| MPG Powder (mg/ml) | 60 |
| Tris (mM) | 30 |
| Methylparaben (w/v, %) | 0.1 |
| Sodium Azide (w/v, %) | 0.095 |
| pH | 8.5 |

TABLE 3-continued

|  | Conc. or pH |
|---|---|
| Lysis Reagent | |
| Guanidine Thiocyanate (M) | 4 |
| Sodium Citrate (mM) | 50 |
| Polydocanol (w/v, %) | 5 |
| Dithiotreitol (w/v, %) | 2 |
| pH | 5.8 |
| Wash buffer | |
| Sodium Citrate (mM) | 7.5 |
| Methylparaben (w/v, %) | 0.1 |
| pH | 4.1 |
| Elution buffer | |
| Tris (mM) | 30 |
| Methylparaben (w/v, %) | 0.2 |
| pH | 8.5 |

After the final step, the process head of the Hamilton Star apparatus adds the respective mastermixes (Mmxs) containing amplification reagents to each well (e.g., the Mmxs disclosed in U.S. Pat. No. 8,609,340), mixes the fluids containing the isolated nucleic acids with the Mmx and transfers each resulting mixture to a corresponding well of a microwell plate in which the amplification is carried out.

For amplification and detection, the microwell plate is sealed with an automated plate sealer and the plate is transferred to the LightCycler 480. The following PCR profile is used:

TABLE 4

Thermo cycling profile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
|  | 94 | None | 00:00:05 | 4.4 |  |  |
|  | 55 | None | 00:02:00 | 2.2 |  |  |
|  | 60 | None | 00:06:00 | 4.4 |  |  |
|  | 65 | None | 00:04:00 | 4.4 |  |  |
| 1st Measurement | 95 | None | 00:00:05 | 4.4 | 5 | Quantification |
|  | 55 | Single | 00:00:30 | 2.2 |  |  |
| 2nd Measurement | 91 | None | 00:00:05 | 4.4 | 45 | Quantification |
|  | 58 | Single | 00:00:25 | 2.2 |  |  |
| Cooling | 40 | None | 00:02:00 | 2.2 | 1 | None |

TABLE 5

Detection Format (Manual)

| Filter Combination | Integration Time (sec) |
|---|---|
| 435-470 | 1 |
| 495-525 | 0.5 |
| 540-580 | 0.5 |
| 610-645 | 0.5 |
| 680-700 | 1 |

PCR cycling is divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Example 3. Evaluation of Thermostability of Armored RNA

Figure 3:
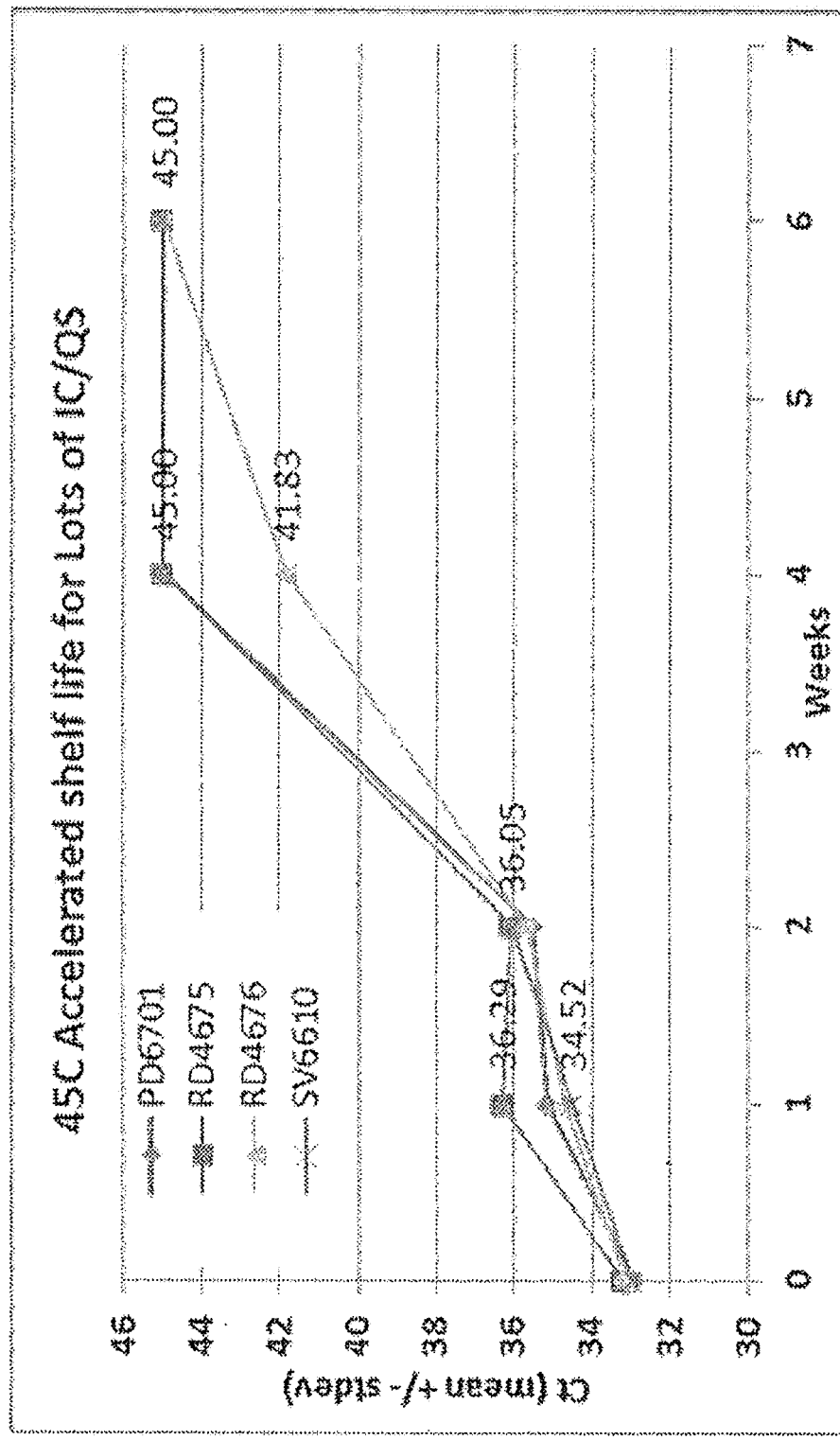
FIG. 3 illustrates the degradation of Armored RNA compositions at elevated temperatures over time.

To test the thermostability of Armored RNA (aRNA), stress tests were performed on various lots of pEF070 aRNA (the following lots were tested: PD6701; RD4675; RD4676; and SV6610). An aliquot of each lot at a pre-determined concentration was stored for an extended period at a range of temperatures (4-45° C.). The results are shown in FIG. 3. At day 0, all four lots exhibited a Ct of approximately 32.5 and over time and extended temperature, the measurable Ct drops rapidly and is completely lost in 3 out of the 4 lots tested by 4 weeks at 45° C.

Example 4. Evaluation of Thermostability of Phi6 Composition

To test the thermostability of Phi6, stress tests were performed on cultures of purified Phi6 in different buffers. Briefly, aliquots of full process controls at pre-determined concentration were stored for an extended period at a range of temperatures (4-45° C.) and evaluated for performance (copy number maintenance). Performance was measured by Ct and amplitude measurements in qPCR.

To establish the concentration, Phi6 was serially diluted to create a dynamic range and Ct and amplitude were calculated on a Cobas® LIAT® analyzer (n=3). Illustrative examples of primer-probe sequence and thermocycling parameters are provided below:

TABLE 6

| Name | Sequence (5'-3') | SEQ ID NO |
|---|---|---|
| Probe | TGCGATCCGTGTCCAAGGGTTCGC | SEQ ID NO: 1 |
| Primer 1 | GCATTTCTGGAGCAGTGCAT | SEQ ID NO: 2 |
| Primer 2 | GACTGCCAAGGTGCCATTA | SEQ ID NO: 3 |

TABLE 7

| | Setting | | |
|---|---|---|---|
| Steps | Temp. (° C.) | Time (sec) | Cycle Number |
| RT | 55 | 30 | 1 |
| | 60 | 60 | |
| | 65 | 115 | |
| PCR1 | 95 | 5 | 5 |
| | 55 | 5 | |
| | 58 | 5 | |
| | 60 | 5 | |
| PCR2 | 91 | 4 | 35 |
| | 58 | 9 | |
| | 60 | 6 + 0.086/cycle | |

Using a Ct of approximately 29.5-30.0, Phi6 was serially diluted into each of the buffer formulations provided in Table 1. After diluting Phi6 in each of the buffers to the Ct range for RNA-based Cobas® assays, single-use sterile aliquots were made for each buffer condition. These single-use aliquots were then stored at temperature-monitored incubators set to 4° C., 30° C., 37° C., and 45° C.

Figure 4A:
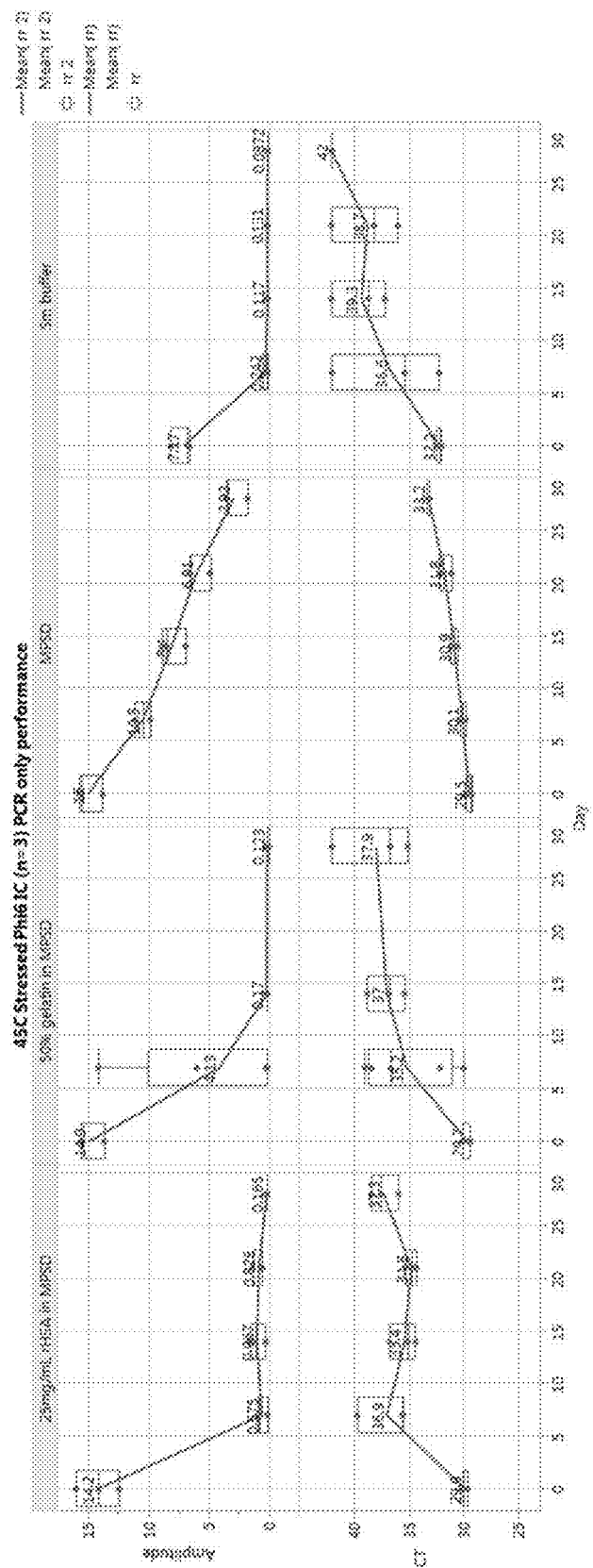
FIGS. 4a-4b shows the thermostability of various Phi6 compositions at elevated temperatures over time.
Figure 4B:
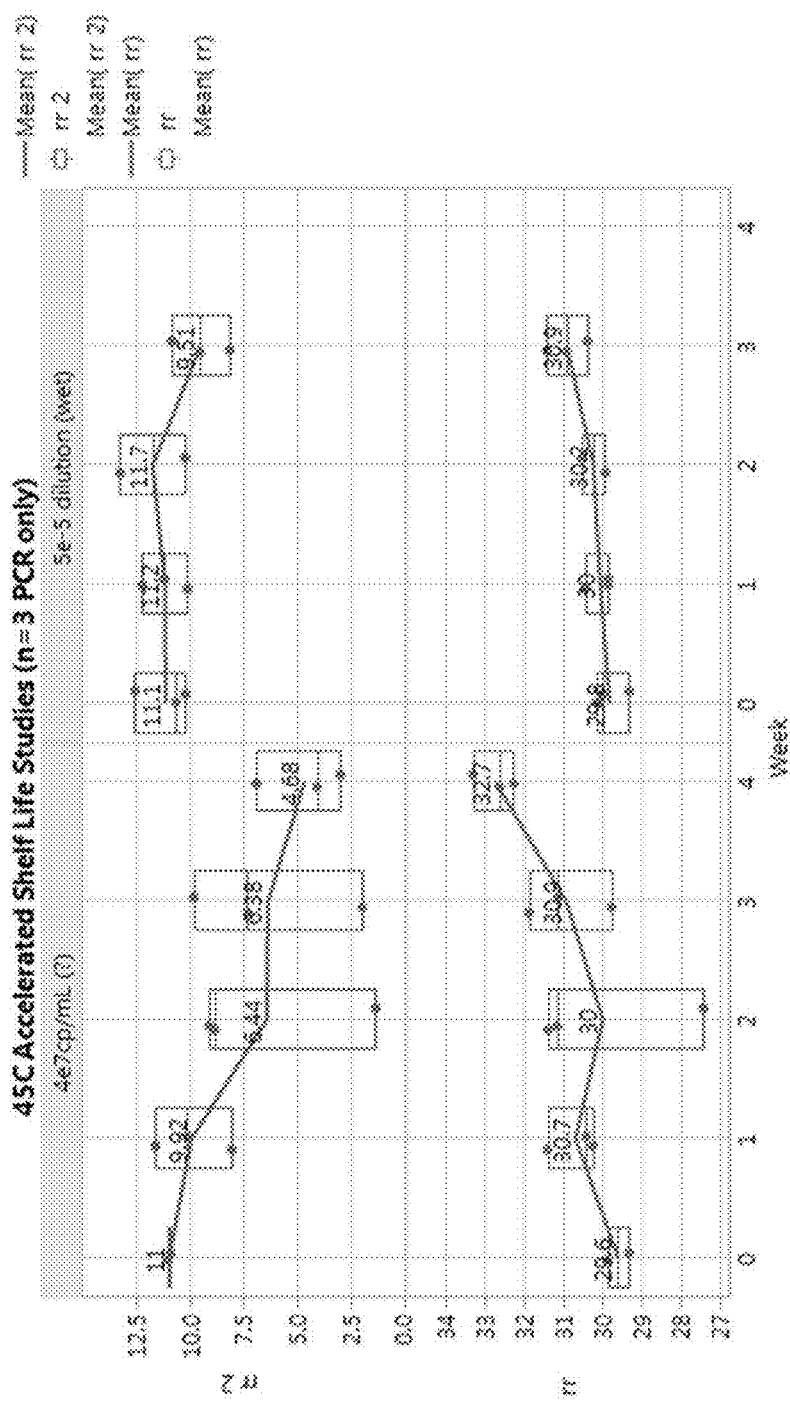

The results are shown in FIG. 4(a) (bottom panel is Ct and top panel is amplitude). The results indicate that when using a Tris-buffer, Phi6 bacteriophage is considerably more stable than the current standard aRNA. In addition, the addition of up to 40% glycerol further improved the thermostability of the Phi6 formulation in accelerated shelf life studied (see FIG. 4(b)).

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed:

1. A device configured to perform a viral load analysis in a sample, said device comprising
   (a) a sample introduction port adapted to receive a sample aliquot;
   (b) an internal control compartment comprising a composition comprising bacteriophage Phi6 suspended in a buffer suitable for a nucleic acid amplification reaction at a pH between 7-9, including a chelating agent and a preservative; and
   (c) a PCR analysis region comprising one or more additional compartments each configured to conduct one or more steps of said PCR analysis comprising reagent preparation, target enrichment, inhibitor removal, nucleic acid extraction, amplification, and real-time detection.

2. The device of claim 1 wherein said sample comprises plasma, whole blood, urine, fecal material, mucus, and combinations thereof.

3. The device of claim 1 further comprises a swab.

4. The device of claim 1 wherein the sample is suspended in universal transport medium.

5. The device of claim 1 wherein said analysis is an HIV viral load analysis.

6. The device of claim 1 wherein said analysis is a hepatitis or cytomegalovirus viral load analysis.

7. The device of claim 6 wherein said hepatitis is hepatitis B or hepatitis C.

8. The device of claim 1 wherein the composition further comprises one or more additional components comprising BSA, gelatin, poly rA RNA, glycerol, amino acids, trehalose, casein, or polyethylene glycol.

9. The device of claim 1 wherein said buffer is selected from a citrate buffer, a glycine buffer, a tricine buffer, PIPES, and HEPES.

10. The device of claim 1 wherein said bacteriophage Phi6 is present at a concentration of up to 4e5 copies/mL.

11. The device of claim 1 wherein the chelating agent is selected from EDTA and EGTA.

12. The device of claim 1 wherein the preservative is selected from sodium azide and ProClin 300.

13. The device of claim 1 wherein the composition comprises
   (a) up to 4e5 cp/mL of Phi6 in 10 mM Tris, pH 8.0, 0.1 mM EDTA, 0.05% Sodium Azide, and 25 mg/mL BSA;
   (b) up to 4e5 cp/mL of Phi6 in 10 mM Tris, pH 8.0, 0.1 mM EDTA, 0.05% Sodium Azide, and 1% gelatin;
   (c) up to 4e5 cp/mL of Phi6 in 10 mM Tris, pH 8.0, 0.1 mM EDTA, 0.05% Sodium Azide, and 20 mg/L poly rA RNA; or
   (d) up to 4e5 cp/mL of Phi6 in 10 mM Tris, pH 8.0, 0.1 mM EDTA, 0.05% Sodium Azide, 20 mg/L poly rA RNA, and 40% glycerol.

14. The device of claim 1 wherein the composition is thermostabile at 45° C. for up to 28 days.

15. The device of claim 1 wherein the composition is thermostabile at 30° C. for up to 110 days.

* * * * *